United States Patent [19]

Kutter et al.

[11] 3,948,898
[45] Apr. 6, 1976

[54] 1,3-DIOXO-2-AMINOALKYL-4,4-DIMETHYL-ISOQUINOLINES AND SALTS THEREOF

[75] Inventors: Eberhard Kutter; Volkard Austel, both of Biberach an der Riss; Wolfgang Eberlein, Mettenberg-Biberach; Joachim Heider, Warthausen-Oberhoefen, all of Germany

[73] Assignee: Boehringer Ingelheim GmbH, Ingelheim am Rhein, Germany

[22] Filed: Sept. 4, 1974

[21] Appl. No.: 503,072

[30] Foreign Application Priority Data
Sept. 8, 1973  Germany............................ 2345422
Sept. 8, 1973  Germany............................ 2345423

[52] U.S. Cl. ........ 260/268 BQ; 260/289 R; 424/258
[51] Int. Cl.² ....................................... C07D 217/16
[58] Field of Search .................. 260/268 BQ, 289 D

[56] References Cited
UNITED STATES PATENTS
3,726,875  4/1973  Kadin ........................... 260/268 BQ
3,870,721  3/1975  Archibald et al. ............... 260/289 D OTHER PUBLICATIONS
Boelhme et al., Chem. Abstr., Vol. 73, 45304a, (1970).

Primary Examiner—Paul M. Coughlan, Jr.
Attorney, Agent, or Firm—Hammond & Littell

[57] ABSTRACT

Compounds of the formula

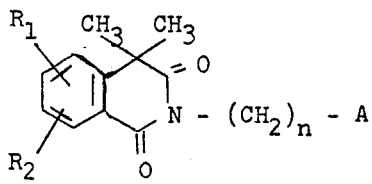

wherein $R_1$ is hydrogen, halogen, methoxy or methylthio
$R_2$ is hydrogen or methoxy,
$n$ is 2 or 3, and
A is

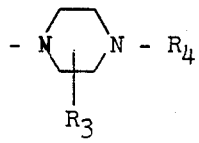

or

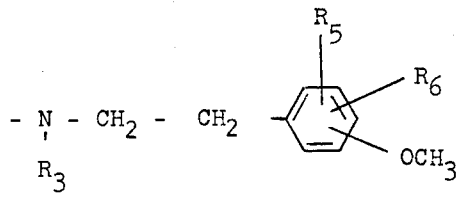

where $R_3$ is hydrogen or methyl,
$R_4$ is pyridyl, methy-pyridyl, phenyl, chlorophenyl, trifluoromethyl-phenyl, tolyl, xylyl, ethyl-phenyl, diethyl-phenyl, methoxy-phenyl or dimethoxy-phenyl, and
$R_5$ and $R_6$, which may be identical to or different from each other, are each hydrogen or methoxy, and non-toxic, pharmacologically acceptable acid addition salts thereof; the compounds as well as the salts are useful as hypotensives, sedatives, antiarrhythmics and bradycardiacs.

2 Claims, No Drawings

1,3-DIOXO-2-AMINOALKYL-4,4-DIMETHYL-ISOQUINOLINES AND SALTS THEREOF

This invention relates to novel 1, 3- dioxo -2- aminoalkyl -4,4- dimethyl-isoquinolines and their non-toxic acid addition salts, as well as to methods of preparing these compounds.

More particularly, the present invention relates to a novel class of isoquinoline derivatives represented by the formula

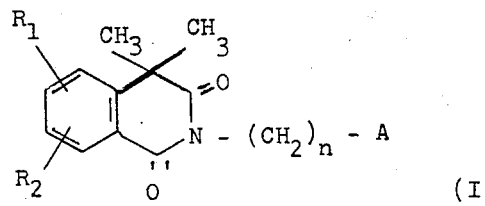

(I)

wherein $R_1$ is hydrogen, halogen, methoxy or methylthio,
$R_2$ is hydrogen or methoxy,
n is 2 or 3, and
A is

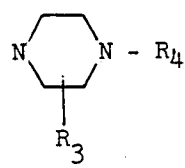

or

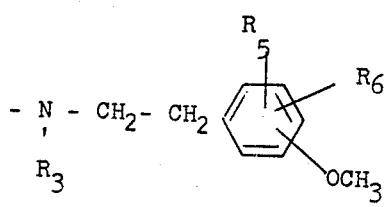

where $R_3$ is hydrogen or methyl,
$R_4$ is pyridyl, methyl-pyridyl, phenyl, chloro-phenyl, trifluoromethyl-phenyl, tolyl, xylyl, ethyl-phenyl, diethyl-phenyl, methroxy-phenyl or drimethoxy-phenyl, and
$R_5$ and $R_6$, which may be identical to or different from each other, are each hydrogen or methoxy, and non-toxic, pharmacologically acceptable acid addition salts thereof.

The compounds embraced by formula I may be prepared by the following methods:

Method A.

By reacting a compound of the formula

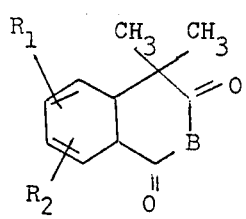

(II)

or

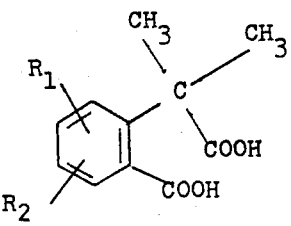

(IIa)

wherein $R_1$ and $R_2$ have the same meanings as in formula I, and
B is oxygen, imino or substituted imino, with an amine of the formula $$NH_2 - (CH_2)_n - A \qquad (III)$$

wherein A and n have the same meanings as in formula I,
or an acid addition salt thereof.

The reaction is preferably carried out in the presence of a solvent, such as glycol, or in the molten state at temperatures from about 50° to 250°C. The addition of a base, such as potassium-tert. butylate is of advantage, especially if the compound of the formula III is used in the form of an acid addition salt.

Method B.

By reacting a N-alkyl-isoquinoline-dione of the formula

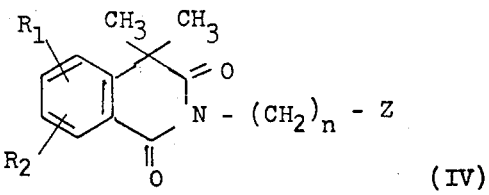

(IV)

wherein $R_1$, $R_2$ and $n$ have the same meanings as in formula I and
Z is a nucleophilically easily exchangeabe group, preferably chlorine, bromine, iodine, alkylsulfonyloxy or arylsulfonyloxy, such as toluenesulfonyloxy,
with an amine of the formula $$H - A \qquad (V)$$

wherein A has the meanings previously defined.

The reaction is preferably carried out in the presence of a solvent, such as in methanol, ether, tetrahydrofuran, methylformamide, dimethylformamide, dimethylsulfoxide or benzene, and advantageously at temperatures between −50° and 250°C depending on the reactivity of Z. The presence of an acid binding agent such as an alcoholate, metal hydroxide, metal oxide or metal carbonate, is of advantage.

Method C.

By reacting a homophthalimide of the formula

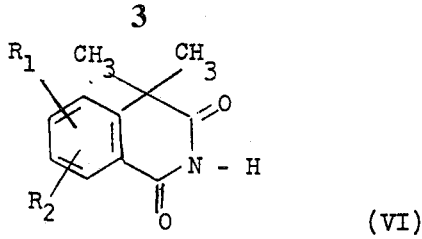

(VI)

wherein $R_1$ and $R_2$ have the same meanings as in formula I, or a metal salt, preferably an alkali metal salt thereof, with a substituted amine of the formula

wherein A, Z and n have the meanings previously defined.

The reaction is preferably carried out in the presence of an acid binding agent, such as an alkali metal alcoholate, a metal oxide, metal hydroxide or metal carbonate, and advantageously in the presence of a solvent, such as methanol, isopropanol, dimethylformamide or dimethylsulfoxide, at temperatures between 0°C and the boiling point of the solvent which is used. If an alkali metal salt of the homophthalimide of the formula VI is used as the starting compound, the presence of an acid binding agent is not required.

The starting compounds embraced by formulas II through VII are either described in the literature or may be prepared by processes described in the literature.

The compounds of the formula I are organic bases and therefore form addition salts with acids. Examples of non-toxic, pharmacologically acceptable acid addition salts are those formed with mineral acids, such as hydrochloric acid, hydrobromic acid, hydriodic acid, hydrofluoric acid, nitric acid, sulfuric acid or phosphoric acid, or organic acids, such as acetic acid, propionic acid, butyric acid, malonic acid, succinic acid, maleic acid, fumaric acid, malic acid, tartaric acid, citric acid, benzoic acid, p-hydroxybenzoic acid, p-aminobenzoic acid, salicylic acid, acetyl-salicyclic acid, phthalic acid terephthalic acid, ascorbic acid, methanesulfonic acid, ethanephosphonic acid, 8-chlorotheophylline or the like.

The following examples illustrate the present invention and will enable others skilled in the art to understand it more completely. It should be understood, however, that the invention is not limited solely to the particular examples given below.

EXAMPLE 1

1-[4,4-Dimethyl-1,3-dioxo-(2H,4H)-isoquinolin-2-yl]-2-(4-phenyl-piperazin-1-yl)-ethane and its dihydrochloride by method A.

19 gm of 1,2,3,4-tetrahydro-4,4-dimethyl-isochromandione-(1,3) and 20.5 gm of 2-(4-phenyl-piperazine-1-yl)-ethyl-amine were refluxed in 150 ml of xylene for 12 hours in an apparatus equipped with a water trap. Subsequently, the solvent was removed, the free base residue was taken up in ether, and the dihydrochloride of the formula

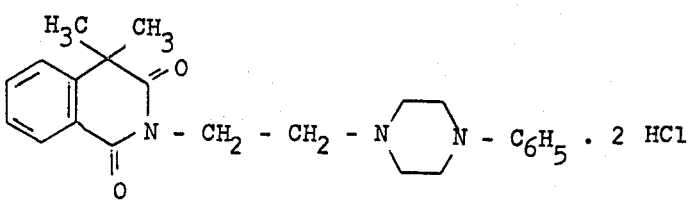

having a melting point of 193° - 205°C (decomp.) after recrystallization from ethanol, was precipitated with ethereal hydrochloric acid.

EXAMPLE 2

1-[4,4-Dimethyl-7-chloro-1,3-dioxo-(2H,4H)-isoquinolin-2-yl]-2-(4-phenyl-piperazin-1-yl)-ethane and its hydrochloride, m.p. 231° - 232°C after recrystallization from isopropanol, were prepared analogous to Example 1 from 1,2,3,4-tetrahydro-7-chloro-4,4-dimethyl-isochromandione-(1,3) and 2-(4-phenyl-piperazin-1-yl)-ethylamine.

EXAMPLE 3

1-[4,4-Dimethyl-7-methoxy-1,3-dioxo-(2H,4H)-isoquinolin-2-yl]-2-(4-phenyl-piperazin-1-yl)-ethane and its hydrochloride, m.p. 215° - 218°C after recrystallization from isopyopanol, were prepared analogous to Example 1 from 1,2,3,4-tetrahydro-7-methoxy-4,4-dimethyl-isochroman-dione-(1,3) and 2-(4-phenyl-piperazin-1-yl)-ethyl-amine, but using glycol as the solvent.

EXAMPLE 4

1-[4,4-Dimethyl-7-fluoro-1,3-dioxo-(2H,4H)-isoquinolin-2-yl]-2-(4-phenyl-piperazin-1-yl)-ethane and its hydrochloride m.p. 200°-203°C after recrystallization from isopropanol, were prepared analogous to Example 3 from 1,2,3,4-tetrahydro-7-fluoro-4,4-dimethyl-isochromandione-(1,3) and 2-(4-phenyl-piperazin-1-yl)-ethylamine.

EXAMPLE 5

1-[4,4-Dimethyl-6,7-dimethoxy-1,3-dioxo-(2H,4H)-isoquinolin-2-yl]-2-[4-(2-methoxy-phenyl)-piperazin-1-yl]-ethane and its hydrochloride, m.p. 264°-265°C after recrystallization from ethanol, were prepared analogous to Example 1 from 1,2,3,4-tetrahydro-6,7-dimethoxy-4,4-dimethyl-isochroman-dione-(1-3) and 2-[4-(2-methoxy-phenyl)-piperazin-1-yl]-ethyl-amine.

EXAMPLE 6

1-[4,4-Dimethyll-1,3-dioxo-(2H,4H)-isoquinolin-2yl]-3-[4-(pyridyl-2)-piperazin-1-yl]-propane and its dihydrochloride, m.p. 176°-178°C after crystallization from acetone, were prepared analogous to Example 1 from 1,2,3,4-tetrahydro-4,4-dimethyl-isochroman-dione(1,3) and 3-[4-(pyridyl-2-piperazin-1-yl]-propyl-amine. The dihydrochloride was precipitated from toluene with ethereal hydrochloric acid.

EXAMPLE 7

1-[4,4-dimethyl-1,3-dioxo-(2H,4H)-isoquinoline-2-yl]-2-[4-(2-methoxy-phenyl)-piperazin-1-yl]-ethane and its dihydrochloride by method B.

A mixture consisting of 5 gm of 2-(2-chloro-ethyl)-4,4-dimethyl-1,2,3,4-tetrahydro-isoquinoline-dione-(1,3), 5.3 gm of 1-(2-methoxy-phenyl)-piperazine dihydrochloride, 50 ml of glycol and 6.75 gm of potassium tert.butylate was heated at 180°C for four hours. Thereafter, the reaction mixtrue was cooled, then diluted with water, and the aqueous mixture was extracted with chloroform. The chloroform phase was washed with water, dried and evaporated, and the residue was purified by column chromatography on silicagel with a mixture of chloroform and methanol (95:5). The main fraction was isolated and evaporated; the residue, i.e. the free base reaction product, was dissolved in isopropanol, the resulting solution was acidified with ethereal hydrochloric acid, and the precipitate formed thereby was recrystallized from isopropanol, yielding the dihydrochloride of the formula

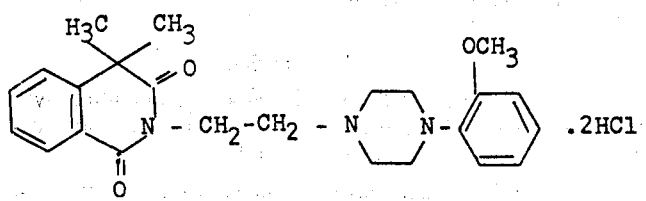

having a melting point of 215°–217°C.

EXAMPLE 8

1-[4,4-Dimethyl-7-methoxy-1,3-dioxo-(2H,4H)-isoquinolin-2-yl]-2-[4-(2-methoxy-phenyl)-piperazin-1-yl]-ethane and its dihydrochloride, m.p. 211°–213°C after recrystallization from isopropanol, were prepared analogous to Example 7 from 2-(2-chloro-ethyl)-4,4-dimethyl-7-methoxy-1,2,3,4-tetrahydro-isoquinoline-dione-(1,3) and 1-(2-methoxyphenyl)-piperazine dihydrochloride.

EXAMPLE 9

1-[4,4-Dimethyl-7-methoxy-1,3-dioxo-(2H,4H)-isoquinolin-2-yl]-3-[4-(2-methoxy-phenyl)-piperazin-1-yl]-propane and its dihydrochloride, m.p. 195°–200°C after recrystallization from ethanol were prepared analogous to Example 7 from 2-(3-chloro-propyl)-4,4-dimethyl-7-methoxy-1,2,3,4-tetrahydro-isoquinoline-dione-(1,3) and 1-(2-methoxyphenyl)-piperazine dihydrochloride.

EXAMPLE 10

1-[4,4-Dimethyl-1,3-dioxo-(2H,4H)-isoquinolin-2-yl]-2-(4-phenyl-3-methyl-piperazin-1-yl)-ethane and its dihydrochloride, m.p. 96°C (decomp.) after recrystallization from isopropanol, were prepared analogous to Example 7 from 2-(2-chloro-ethyl)-4,4-dimethyl-1,2,3,4-tetrahydro-isoquinoline-dione-(1,3) and 1-phenyl-2-methyl-piperazine, but without potassium tert. butylate.

EXAMPLE 11

1-[4,4-Dimethyl-1,3-dioxo-(2H,4H)-isoquinolin-2-yl]-2-[4-(4-methoxy-phenyl)-piperazin-1-yl]-ethane and its dihydrochloride, m.p. 228°C (decomp.) after recrystallization from isopropanol, were prepared analogous to Example 7 from 2-(2-chloro-ethyl)-4,4-dimethyl-1,2,3,4-tetrahydro-isoquinoline-dione-(1,3) and 1-(4-methoxyphenyl)-piperazine, but without potassium ter.butylate.

EXAMPLE 12

1-[4,4-Dimethyl-1,3-dioxo-(2H,4H)-isoquinolin-2-yl]-2-[4-(4-chloro-phenyl)-piperazin-1-yl]-ethane and its dihydrochloride, m.p. 135°C (decomp.) after recrystallization from isopropanol, were prepared analogous to Example 7 from 2-(2-chloro-ethyl)-4,4-dimethyl-1,2,3,4-tetrahydro-isoquinoline-dione-(1,3) and 1-(4-chloro-phenyl)-piperazine dihydrochloride.

EXAMPLE 13

1-[4,4-Dimethyl-1,3-dioxo-(2H,4H)-isoquinolin-2-yl]-2-[4-(3-trifluortomethyl-phenyl)-piperazin-1-yl]-ethane and its hydrochloride, m.p. 230°C after recrystallization from isopropanol, were prepared analogous to Example 7 from 2-(2-chloro-ethyl)-4,4-dimethyl-1,2,3,4-tetrahydroisoquinoline-dione-(1,3) and 1-(3-trifluoromethyl-phenyl)piperazine with one equivalent of potassium tert.butylate.

EXAMPLE 14

1-[4,4-Dimethyl-1,3-dioxo-(2H,4H)-isoquinolin-2-yl]-2-[4-(2,6-dimethyl-phenyl)-piperazin-1-yl]-ethane and its hydrochloride, m.p. 230°C (decomp.) after recrystallization from isopropanol/ether, were prepared analogous to Example 7 from 2-(2-chloro-ethyl)-4,4-dimethyl-1,2,3,4-tetrahydro-isoquinoline-dione-(1,3) and 1-(2,6-dimethylphenyl)-piperazine with one equivalent of potassium tert. butylate.

EXAMPLE 15

1-[4,4-Dimethyl-1,3-dioxo-(2H,4H)-isoquinolin-2-yl]-2-[4-(2-chloro-phenyl)-piperazin-1-yl]-ethane and its hydrochloride, m.p. 228°C after recrystallization from isopropanol/ether, were prepared analogous to Example 7 from 2-(2-chloro-ethyl)-4,4-dimethyl-1,2,3,4-tetrahydro-isoquinoline-dione-(1,3) and 1-(2-chloro-phenyl)-piperazine hydrochloride hydrate with 2 equivalents of potassium tert. butylate.

EXAMPLE 16

1-[4,4-Dimethyl-1,3-dioxo-(2H,4H)-isoquinolin-2-yl]-3-[4-(3-trifluoromethyl-phenyl)-piperazin-1-yl]-propane and its hydrochloride, m.p. 215°–220°C after crystallization from methanol-/ethereal hydrochloric acid, were prepared analogous to Example 7 from 2-(3-chloro-propyl)-4,4-dimethyl-1,2,3,4-tetrahydro-isoquinoline-dione-(1,3) and 1-(3-trifluoromethyl-phenyl)-piperazine with one equivalent of potassium tert.butylate.

EXAMPLE 17

1-[4,4-Dimethyl-1,3-dioxo-(2H,4H)-isoquinolin-2-yl]-2-[4-(3,4-dimethoxy-phenyl)-piperazin-1-yl]-ethane and its dihydrochloride, m.p. 158°C (decomp.) after crystallization from methanol/ethereal hydrochloric acid, were prepared analogous to Example 7 from 2-(2-chloro-ethyl)-4,4-dimethyl-1,2,3,4-tetrahydro-isoquinoline-dione-(1,3) and 1-(3,4-dimethoxy-phenyl)-piperazine with one equivalent of potassium tert.butylate.

EXAMPLE 18

1-[4,4-Dimethyl-1,3-dioxo-(2H,4H)-isoquinolin-2-yl]-2-[4-(2-methyl-phenyl)-piperazin-1-yl]-ethane and its hydrochloride, m.p. 247°C (decomp.) after recrystallization from isopropanol/ether, were prepared analogous to Example 7 from 2-(2-chloro-ethyl)-4,4-dimethyl-1,2,3,4-tetrahydro-isoquinoline-dione-(1,3) and 1-(2-methyl-phenyl)-piperazine dihydrochloride.

EXAMPLE 19

1-[4,4-Dimethyl-1,3-dioxo-(2H,4H)-isoquinolin-2-yl]-2-[4-(2-ethyl-phenyl)-piperazin-1-yl]-ethane and its dihydrochloride, m.p. 188°–192°C after recrystallization from methanol/ether, were prepared analogous to Example 7 from 2-(2-chloro-ethyl)-4,4-dimethyl-1,2,3,4-tetrahydro-isoquinoline-dione-(1,3) and 1-(2-ethyl-phenyl)-piperazine with one equivalent of potassium tert.butylate.

EXAMPLE 20

1-[4,4-Dimethyl-6,7-dimethoxy-1,3-dioxo-(2H,4H)-isoquinolin-2-yl]-3-[4-(2-methoxy-phenyl)-piperazin-1-yl]-propane and its hydrochloride, m.p. 198°–202°C(decomp) after recrystallization from methanol/ether, were prepared analogous to Example 7 from 2-(3-chloro-propyl)-4,4-dimethyl-6,7-dimethoxy-1,2,3,4-tetrahydro-isoquinoline-dione-(1,3) and 1-(2-methoxy-phenyl)-piperazine-dihydrochloride.

EXAMLE 21

1-[4,4-Dimethyl-1,3-dioxo-(2H,4H)-isoquinolin-2-yl]-3-[4-(2-methoxy-phenyl)-piperazin-1-yl]-propane and its hydrochloride, m.p. 235°–237°C after recrystallization from ethanol, were prepared analogous to Example 7 from 2-(3-chloro-propyl)-4,4-dimethyl-1,2,3,4-tetrahydro-isoquinoline-dione-(1,3) and 1-(2-methoxy-phenyl)-piperazine dihydrochloride.

EXAMPLE 22

1-[4,4-Dimethyl-7-methoxy-1,3-dioxo-(2H,4H)-isoquinolin-2-yl]-3-[4-(pyridil-2)-piperazin-1-yl]-propane and its dihydrochloride, m.p. 193°–196°C, were prepared analogous to Example 7 from 2-(3-chloro-propyl)-4,4-dimethyl-7-methoxy-1,2,3,4-tetrahydro-isoquinoline-dione-(1,3) and 1-[pyridyl-(2)]-piperazine with one equivalent of potassium tert. butylate.

EXAMPLE 23

1-[4,4-Dimethyl-7-methoxy-1,3-dioxo-(2H,4H)-isoquinolin-2-yl]-3-[4-(6-methyl-pyridyl-2)-piperazin-1-yl]-propane and its dihydrochloride, m.p. 172°–176°C after recrystallization from ethanol/ether, were prepared analogous to Example 7 from 2-(3-chloro-propyl)-4,4-dimethyl-7-methoxy-1,2,3,4-tetrahydro-isoquinoline-dione-(1,3) and 1-[6-methyl-pyridyl-(2)]-piperazine with one equivalent of potassium tert.butylate.

EXAMPLE 24

1-[4,4-Dimethyl-1,3-dioxo-(2H,4H)-isoquinolin-2-yl]-3-[4-(6-methyl-pyridyl-2)-piperazin-1-yl]-propane and its hydrochloride, m.p. 88°C (decomp.) after crystallization from methanol with etheral hydrochloric acid, were prepared analogous to Example 7 from 2-(3-chloro-propyl)-4,4-dimethyl-1,2,3,4-tetrahydro-isoquinoline-dione-(1,3) and 1-[6-methylpyridyl-(2)]-piperazine with one equivalent of potassim tert. butylate.

EXAMPLE 25

1-[4,4-Dimethyl-1,3-dioxo(2H,4H)-isoquinolin-2-yl]-3-[4-phenyl-piperazin-1-yl]-propane and its hydrochloride by method C.

4.9 gm of 3-(4-phenyl-piperazin-1-yl)-propyl chloride hydrochloride were dissolved in the least possible quantity of water, the solution was vigorously shaken with a mixture of 100 ml of a saturated aqueous potassium carbonate solution and 100 ml of toluene, and the toluene phase was separated and dried over magnesium sulfate. The toluene solution obtained after filtration was added dropwise to a solution of 3.8 gm of 1,2,3,4-tetrahydro-4,4-dimethyl-1,3-dioxo-(2H,4H)-isoquinoline and 2.6 gm of potassium tert. butylate in 100 ml of dimethylformamide at 70°C over a period of one hour. Subsequently, the mixture was stirred for 2 hours more at that temperature. After removing the solvent, the oily residue was admixed with water, the mixture was extracted with ether several times, the combined etheral extracts were dried over anhydrous calcium chloride and filtered, ethereal hydrochloric acid was added to the filtrate, and the precipitate formed hereby was recrystallized from isopropanol, yielding the hydrochloride of the formula

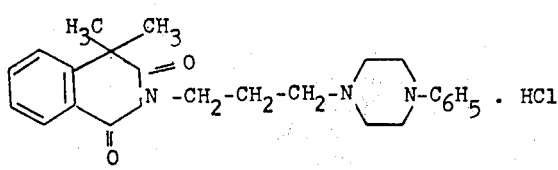

having a melting point of 235°–238°C (decomp.)

EXAMPLE 26

1-[4,4-Dimethyl-7-methoxy-1,3-dioxo-(2H,4H)-isoquinolin-2-yl]-2-[2-(3,4-dimethoxy-phenyl)-ethyl-amino]-ethane and its hydrochloride by method B.

A mixture of 8,5 gm of 2-(2-chloro-ethyl)-4,4-dimethyl-7-methoxy-1,2,3,4-tetrahydro-isoquinoline-dione-(1,3) and 13,6 gm of 3,4-dimethoxyphenyl-ethylamine was heated for 4 hours on an oil bath at a bath temperature of 180°C. Subsequently, water was added. the mixture was extracted with chloroform, and the chloroform phase was washed with water, dried and evaporated. Then, the raw free base reaction product was purified by column chromatography (silicagel column; chloroform/methanol = 95/5), the main fraction was isolated, and the hydrochloride was precipitated by addition of ethereal hydrochloric acid, yielding the compound of the formula

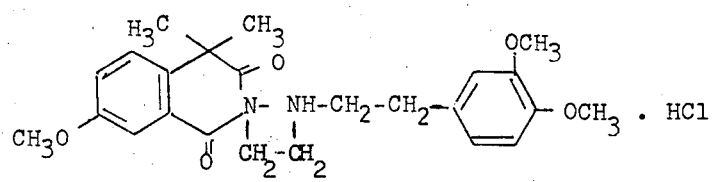

having a melting point of 263°–265°C after recrystallization from ethanol.

EXAMPLE 27

1-[4,4-Dimethyl-1,3-dioxo-(2H,4H)-isoquinolin-2-yl]-2-[2-(3,4-dimethoxy-phenyl)-ethylamino]-ethane and its hydrochloride, m.p. 148°–151°C after recrystallization from ethanol, were prepared analogous to Example 26 from 2-(2-chloro-ethyl)-4,4-dimethyl-1,2,3,4-tetrahydro-isoquinoline-dione-(1,3) and 3,4-dimethoxy-phenyl-ethylamine.

EXAMPLE 28

1-[4,4-Dimethyl-7-methoxy-1,3-dioxo-(2H,4H)-isoquinolin-2-yl]-2-[N-methyl-2-(3,4-dimethoxy-phenyl)-ethylamino]-ethane and its hydrochloride, m.p. 138°–140°C, were prepared analogous to Example 26 from N-methyl-N-[2-(3,4-dimethoxyphenyl)-ethyl]-amine and 2-(2-chloro-ethyl)-4,4-dimethyl-7-methoxy 1,2,3,4-tetrahydro-isoquinoline-dione-(1,3).

EXAMPLE 29

1-[4,4-Dimethyl-1,3-dioxo-(2H,4H)-isoquinolin-2-yl]-3-[N-methyl-N-(2-(3,4-dimethoxy-phenyl)-ethyl-)amino]-propane, A viscous oil, was prepared analogous to Example 26 from 2-(3-chloro-propyl)-4,4-dimethyl-1,2,3,4-tetrahydroisoquinoline-dione-(1,3) and N-methyl-2-(3,4-dimethoxyphenyl)-ethylamine.

EXAMPLE 30

1-[4,4-Dimethyl-7-methoxy-1,3-dioxo-(2H,4H)-isoquinolin-2-yl]-3-[N-methyl-2-(3,4-dimethoxy-phenyl)-ethylamino]propane, a viscous oil, was prepared analogous to Example 29 from 2-(3-chloro-propyl)-4,4-dimethyl-7-methoxy-1,2,3,4-tetrahydro-isoquoline-dione-(1,3) and N-methyl-2-(3,4-dimethoxy-phenyl)-ethylamine.

EXAMPLE 31

1-[4,4-Dimethyl-7-methoxy-1,3-dioxo-(2H,4H)-isoquinolin-2-yl]-3-[2-(3,4,5-trimethoxy-phenyl)-ethylamino]-propane and its hydrochloride, m.p. 157°–159°C after recrystallization from isopropanol, were prepared analogous to Example 26 from 2-(3,4,5-trimethoxy-phenyl)-ethylamine and 2-(3-chloro-propyl)-4,4-dimethyl-7-methoxy-1,2,3,4-tetrahydroisoquinoline-dione-(1,3).

EXAMPLE 32

1-[4,4-Dimethyl-7-methoxy-1,3-dioxo-(2H,4H)-isoquinolin-2-yl]-3-[2-(4-methoxy-phenyl)-ethylamino]-propane and its hydrochloride, m.p. 175°–176°C after recrystallization from isopropanol, were prepared analogous to Example 26 from 2-(3-chloro-propyl)-4,4-dimethyl-7-methoxy-1,2,3,4-tetrahydro-isoquinoline-dione-(1,3) and 2-(4-methoxy-phenyl)ethylamine.

EXAMPLE 33

1-[4,4-Dimethyl-1,3-dioxo-(2H,4H)-isoquinolin-2-yl]-3-[2-(3,4-dimethoxy-phenyl)-ethylamino]-propane and its hydrochloride, m.p. 162°–165°C after recrystallization from isopropanol, were prepared analogous to Example 26 from 2-(3-chloro-propyl)-4,4-dimethyl-1,2,3,4-tetrahydro-isoquinoline-dione-(1,3) and 2-(3,4-dimethoxy-phenyl)-ethylamine.

EXAMPLE 34

1-[4,4-Dimethyl-7-methoxy-1,3-dioxo-(2H,4H)-isoquinolin-2-yl]-3-[2-(3,4-dimethoxy-phenyl)-ethylamino]-propane and its hydrochloride by method A.

a. 2-[2-(3,4-Dimethoxy-phenyl)-ethylamino]-1-cyano-ethane 54.5 gm of 2-(3,4-dimethoxy-phenyl)-ethylamine were dissolved in 100 ml of methanol, a solution of 16.2 gm of acrylonitrile in 50 ml of methanol was added dropwise at 50°C, and the mixture was stirred for 1 hour at 50°C. After evaporation of the methanol, the raw reaction oriduct thus obtained was used without further purification in the next step.

b. 1-[2-(3,4-Dimethoxy-phenyl)-ethylamino]-3-amino-propane

The raw reaction product (70.3 gm) obtained in the preceding step was taken up in 1.3 liters of methanolic ammonia and the mixture was hydrogenated in an autoclave with presence of Raney nickel as the catalyst at 80°C and 50 atmospheres, yielding the above named 1,3-diamino-propane having a boiling point of 168°–173°C at 1 mm Hg.

c. 13,2 gm of 4,4-dimethyl-7-methoxy-1,2,3,4-tetrahydroisochroman-dione-(1,3) and 14.3 gm of 1-[2-(3,4-dimethoxy-phenyl)-ethylamino]-3-amino-propane were boiled in 250 ml of toluene for 5 hours in an apparatus equipped with a water trap. After cooling, the hydrochloride was precipitated from the reaction solution with ethereal hydrochloric acid, and the oily product was recrystallized from ethanol, yielding 1-[4,4-Dimethyl-7-methoxy-1,3-dioxo-(2H,4H)-isoquinolin-2-yl]-3-[2-(3,4-dimethoxy-phenyl)-ethylamino] propane hydrochloride having a melting point of 191°–193°C.

EXAMPLE 35

1-[4,4-Dimethyl-6,7-dimethoxy-1,3-dioxo-(2H,4H)-isoquinolin-2-yl]-3-[2-(3,4-dimethoxy-phenyl)-ethylamino]-propane and its hydrochloride, m.p. 98° – 101°C after recrystallization from ethyl acetate, were prepared analogous to Example 34 from 4,4-dimethyl-6,7-dimethoxy-1,2,3,4-tetrahydro-isochroman-dione-(1,3) and 1-[2-(3,4-dimethoxy-phenyl))ethylamino]-3-amino-propane.

EXAMPLE 36

1-[4,4-Dimethyl-6,7-dimethoxy-1,3-dioxo-(2H,4H)-isoquinolin-2-yl]-3-[N-methyl-2-(3,4-dimethoxy-phenyl)-ethylamino]propane and its hydrochloride, m.p. 167° – 168°C, were prepared analogous to Example 34 from 4,4-dimethyl-6,7-dimethoxy-1,2,3,4-tetrahydro-isochroman-dione-(1,3) and 1-[N-methyl-2-(3,4-dimethoxyphenyl)-ethylamino]-3-amino-propane.

EXAMPLE 37

1-[4,4-Dimethyl-7-methylmercapto-1,3-dioxo-(2H,4H)-isoquinolin-2-yl]-3-[2-(3,4-dimethoxy-phenyl)-ethylamino]propane and its hydrochloride, m.p. 133° – 135°C after recrystallization from ethanol, were prepared analogous to Example 34 from 4,4-dimethyl-7-methylmercapto-1,2,3,4-tetrahydro-isochroman-dione-(1,3) and 1-[2-(3,4-dimethoxy-phenyl)-ethylamino]-3-amino-propane.

EXAMPLE 38

1-[4,4-Dimethyl-7-chloro-1,3-dioxo-(2H,4H)-isoquinolin-2-yl]-3-[2-(3,4-dimethoxy-phenyl)-ethylamino]-propane and its hydrochloride, m.p. 222° – 226°C after recrystallization from ethanol, were prepared analogous to Example 34 from 4,4-dimethyl-7-chloro-1,2,3,4-tetrahydro-isochroman-dione-(1,3) and 1-[2-(3,4-dimethoxy-phenyl)-ethylamino]-3-amino-propane.

The compounds of the present invention, that is, those embraced by formula I and their non-toxic acid addition salts, have useful properties; more particularly, they exhibit mainly hypotensive activity as well as bradycardiac, antiarrhythmic and sedative activities in warm blooded animals, such as dogs.

The hypotensive activity of the compounds of the present invention was ascertained in 2 to 4 mongrel dogs of male and female sex (body weight between 14 and 23 kg) under chloralose-urethane-nembutal anesthesia (54+270+10 mg/kg i.v.). The test compounds were injected intravenously into the vena saphena in aqueous solution. The arterial bloodpressure was measured before and after administration in the arteria femoralis by means of a Stathan-pressure transducer and registered on a Grass-polygraph.

The following table shows illustrative, representative results obtained from these tests, where A = 1-[4,4-Dimethyl-1,3-dioxo-(2H,4H)-isoquinolin-2-yl]-2-[4-(2-methoxy-phenyl)-piperazin-1-yl]-ethane dihydrochloride, and B = 1-[4,4-Dimethyl-7-methoxy-1,3-dioxo-(2H,4H)-isoquinolin-2-yl]-3-[2-(3,4-dimethoxy-phenyl)-ethylamine]propane hydrochloride.

| Compound | Dose mg/kg i.v. | Decrease of bloodpressure mm Hg syst./diast. | Duration of activity in minutes |
|---|---|---|---|
| A | 0.05 | −27/−31 | 53 |
| A | 0.1 | −33/−34 | 47 |
| B | 0.5 | −32/−36 | 35 |
| B | 1.0 | −36/−40 | 40 |

The acute toxicity of the compounds was tested in mice (observation time: 14 days) after oral application. The $LD_{50}$ was calculated from the percentage of the animals which died within the observation time after application of varying doses [see J. Pharmacol. exper. Therap. 96, 99 (1949)]:

| Compound | $LD_{50}$ mg/kg p.o. |
|---|---|
| A | 850 |
| B | 775 |

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.3 to 5.0 mgm/kg body weight, preferably 0.4 to 3.4 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 39

Tablets.

The tablet composition is compounded from the following ingredients:

| | |
|---|---|
| 1-[4,4-Dimethyl-7-methoxy-1,3-dioxo-(2H,4H)-isoquinolin-2-yl]-3-[2-(3,4-dimethoxy-phenyl)-ethylamino]-propane hydrochloride | 100.0 parts |
| Lactose | 50.0 " |
| Polyvinylpyrrolidone | 5.0 " |

-continued

| | |
|---|---|
| Carboxymethyl cellulose | 19.0 " |
| Magnesium stearate | 1.0 " |
| Total | 175.0 parts |

Preparation:

The isoquinoline compound and the lactose are intimately admixed with each other, the mixture is homogeneously moistened with an aqueous solution of the polyvinylpyrrolidone, the moist mass is granulated by passing it through a screen, and the granulate is dried. The dry granulate is then admixed with the remaining ingredients, and the composition is compressed into 175 mgm-tablets in a conventional tablet making machine. Each tablet contains 100 mgm of the isoquinoline compound and is an oral dosage unit composition with effective hypotensive action.

EXAMPLE 40

Coated pills.

The pill core composition is pompounded from the following ingredients:

| | |
|---|---|
| 1-[4,4-Dimethyl-1,3-dioxo-(2H,4H)-isoquinolin-2-yl]-2-[4-(2-chloro-phenyl)-piperazin-1-yl]ethane hydrocloride | 50.0 parts |
| Corn starch, dry | 20.0 " |
| Soluble starch | 2.0 " |
| Carboxymethyl cellulose | 7.0 " |
| Magnesium sterate | 1.0 " |
| Total | 80.0 parts |

Preparation:

The isoquinoline compound and the corn starch are admixed with each other, the mixture is moistened with an aqueous solution of the soluble starch and then granulated by passing it through a screen, the granulate is dried and admixed with the remaining ingredients, and the composition is compressed into 80 mgm-pill cores which are subsequently coated with a thin shell consisting essentially of a mixture of sugar and talcum. The coated pills are finally polished with beeswax. Each coated pill contains 50 mgm of the isoquinoline compound and is an oral dosage unit composition with effective hypotensive action.

EXAMPLE 41

Suppositories

The suppository composition is compounded from the following ingredients:

| | |
|---|---|
| 1-[4,4-Dimethyl-1,3-dioxo-(2H,4H)-isoquinolin-2-yl]-3-[4-(6-methyl-pyridyl-2)-piperazin-1-yl]-propane hydrochloride | 150.0 parts |
| Suppository base (e.g.cocoa butter) | 1550.0 " |
| Total | 1700.0 parts |

Preparation:

The suppository base is melted, the isoquinoline compound is homogeneously blended into the molten mass with the aid of an immersion homogenizer, and 1700 mgm-portions of the composition are poured into cooled suppository molds and allowed to harden therein. Each suppository contains 150 mgm of the isoquinoline compound and is a rectal dosage unit composition with effective hypotensive action.

EXAMPLE 42

Aqueous suspension.

The suspension is compounded from the following ingredients:

| | |
|---|---|
| 1-[4,4-Dimethyl-1,3-dioxo-(2H,4H)-isoquinolin-2-yl]-2-[4-(2-methyl-phenyl)-piperazin-1-yl]-ethane hydrochloride | 5.0 parts |
| Carboxymethyl cellulose | 0.1 " |
| Methyl p-hydroxy-benzoate | 0.05 " |
| Propyl p-hydroxy-benzoate | 0.01 " |
| Sugar | 10.0 " |
| Glycerin | 5.0 " |
| Sorbitol, aqueous 70% solution | 20.0 " |
| Flavoring | 0.3 " |
| Distilled water q.s.ad | 100.0 "by vol. |

Preparation:

The distilled water is heated to 70°C, and the p-hydroxy-benzoates, the glycerin and the carboxymethyl cellulose are dissolved therein while stirring. The resulting solution is cooled to room temperature, the isoquinoline compound is homogeneously suspended therein, and the sugar, the sobitol solution and the flavoring are stirred in. Finally, the suspension is de-aerated by stirring in vacuo. 5 ml of the suspension contains 250 mgm of the isoquinoline compound and are an oral dosage unit composition with effective hypotensive action.

Analogous results are obtained when any one of the other isoquinoline compounds embraced by formula I or a nontoxic acid addition salt thereof is substituted for the particular isoquinoline derivative in Examples 39 through 42. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

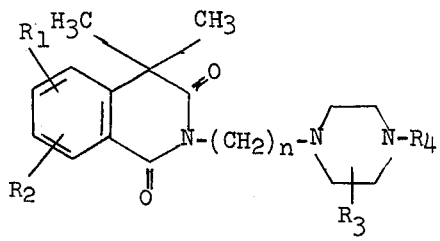

wherein $R_1$ is hydrogen, halogen, methoxy or methylthio, $R_2$ is hydrogen or methoxy, $n$ is 2 or 3, $R_3$ is hydrogen or methyl, and $R_4$ is pyridyl, methyl-pyridyl, phenyl, chlorophenyl, trifluoromethyl-phenyl, tolyl, xylyl, ethyl-phenyl, diethyl-phenyl, methoxy-phenyl or dimethoxy-phenyl, or a non-toxic, pharmacologically acceptable acid addition salt thereof.

2. A compound of claim 1, which is 1-[4,4-dimethyl-1,3-dioxo-(2H,4H)-isoquinolin-2-yl]-2-[4-(2-methoxy-phenyl)piperazin-1-yl]-ethane or a non-toxic, pharmacologically acceptable acid addition salt thereof.

* * * * *